US00PP21099P3

(12) United States Plant Patent
Joubert

(10) Patent No.: US PP21,099 P3
(45) Date of Patent: Jun. 29, 2010

(54) AVOCADO TREE NAMED 'MALUMA'
(50) Latin Name: *Persea americana Mill*
Varietal Denomination: Maluma

(75) Inventor: Andries G. Joubert, Levubu (ZA)

(73) Assignee: A.H. Ernst & Sons (PTY) Ltd., Tzaneen, Limpopo (ZA)

( * ) Notice: Subject to any disclaimer, the term of this patent is extended or adjusted under 35 U.S.C. 154(b) by 0 days.

(21) Appl. No.: 12/290,341

(22) Filed: Oct. 28, 2008

(65) Prior Publication Data

US 2010/0107288 P1 Apr. 29, 2010

(51) Int. Cl.
*A01H 5/00* (2006.01)

(52) U.S. Cl. ..... Plt./200

(58) Field of Classification Search ..... Plt./200
See application file for complete search history.

(56) References Cited

OTHER PUBLICATIONS

Upov Plant Variety Database 2009/03. 2 pages.*

* cited by examiner

*Primary Examiner*—Annette H Para
(74) *Attorney, Agent, or Firm*—Michelle Bos

(57) ABSTRACT

'Maluma' avocado (*Persea americana* Mill.) is notable for its early bearing, precociousness and high yield. The fruit of 'Maluma' is larger and slightly more pyrifom than 'Hass', and is less prone to skin blemishes.

4 Drawing Sheets

Latin name: *Persea americana* Mill.
Variety denomination: 'Maluma'.

BACKGROUND OF THE VARIETY

'Maluma' is a new and distinct variety of avocado tree *Persea americana* Mill. This new variety originated as a chance seedling discovered by the inventor in a cultivated avocado orchard. Although the parentage of the new variety is not known, it appears to be a 'Hass' (U.S. Plant Patent No. 139) type avocado, related to Guatemalan avocado varieties, with some Mexican avocado genetics. 'Maluma' was first observed at a farm located at Levubu, Limpopo Province, Republic of South Africa, and was selected because of its large, early fruit as compared to the surrounding trees. 'Maluma' was first asexually reproduced at Tzaneen, Limpopo Province, in the late 1990s by grafting onto clonal 'Duke 7' (not patented) rootstock and has since been observed to remain true to type over successive asexually propagated generations.

BRIEF DESCRIPTION OF THE VARIETY

'Maluma' was first noted and selected for its early bearing, precociousness and high yield. The fruit of 'Maluma' is larger and slightly more pyrifom than 'Hass', and is less prone to skin blemishes.

BRIEF DESCRIPTION OF THE PHOTOGRAPHS

Figure 1:
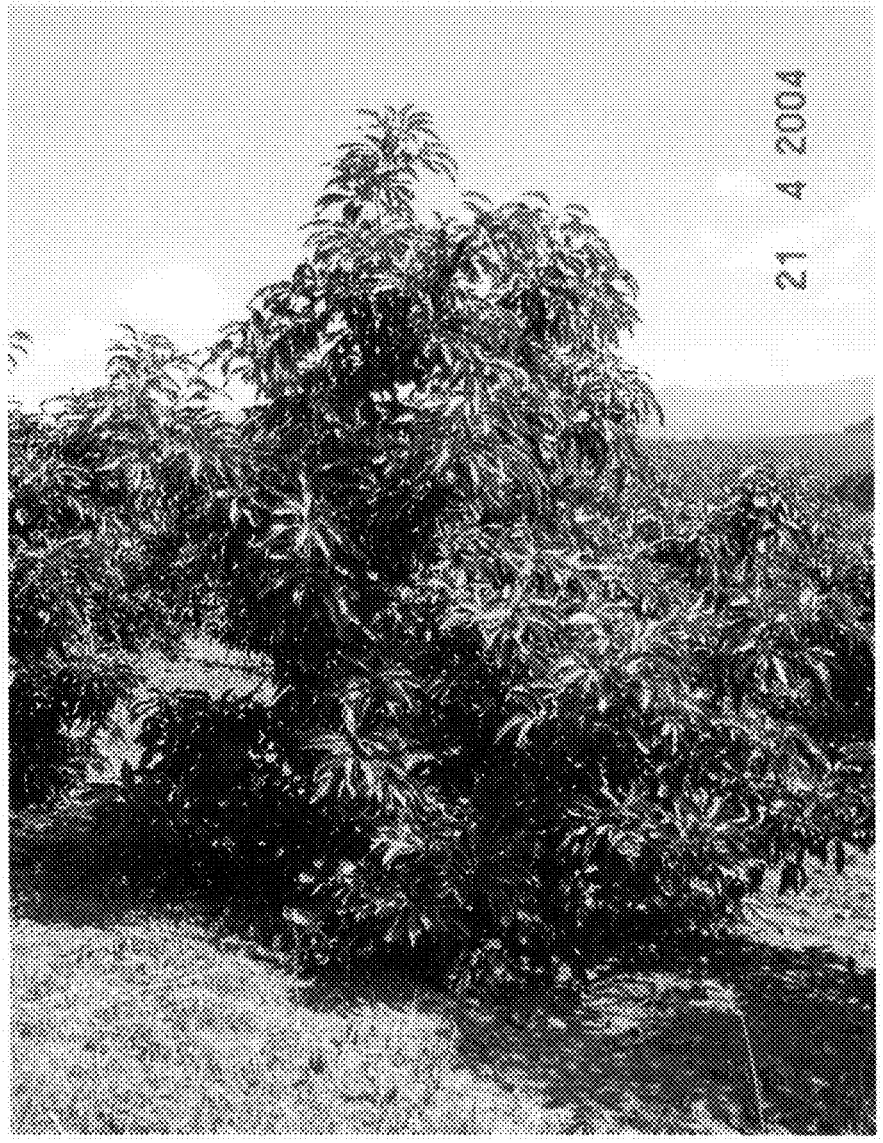
Figure 2:
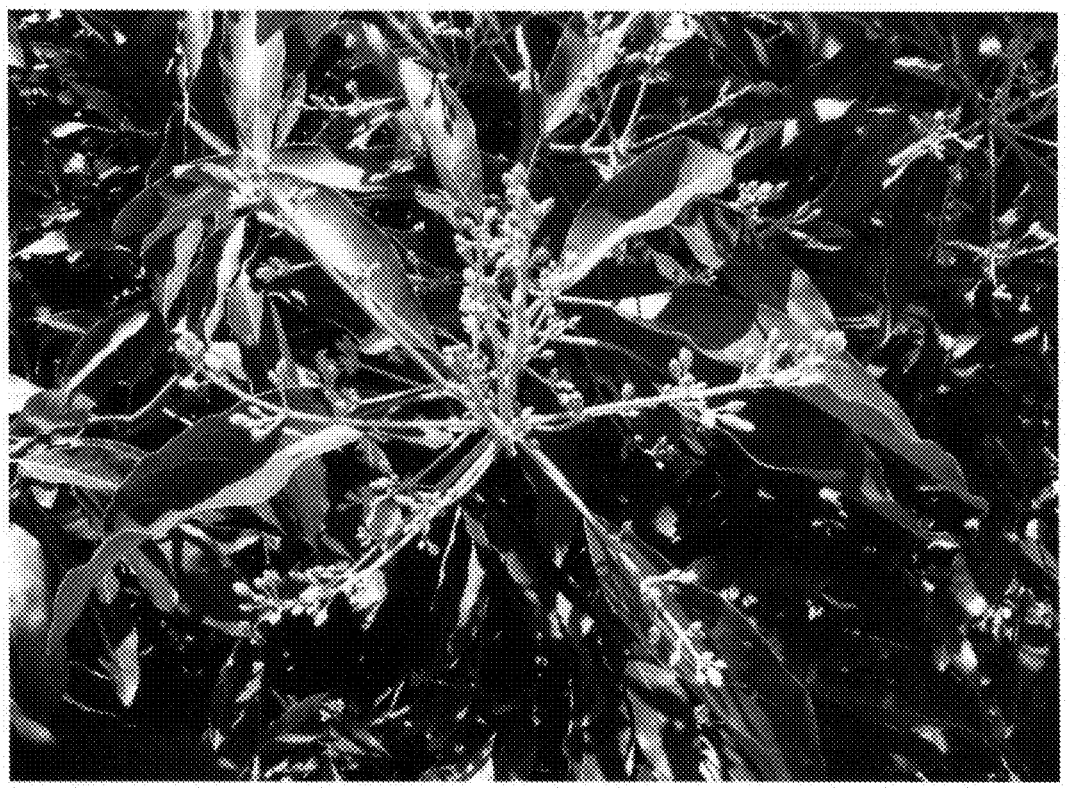
Figure 3:
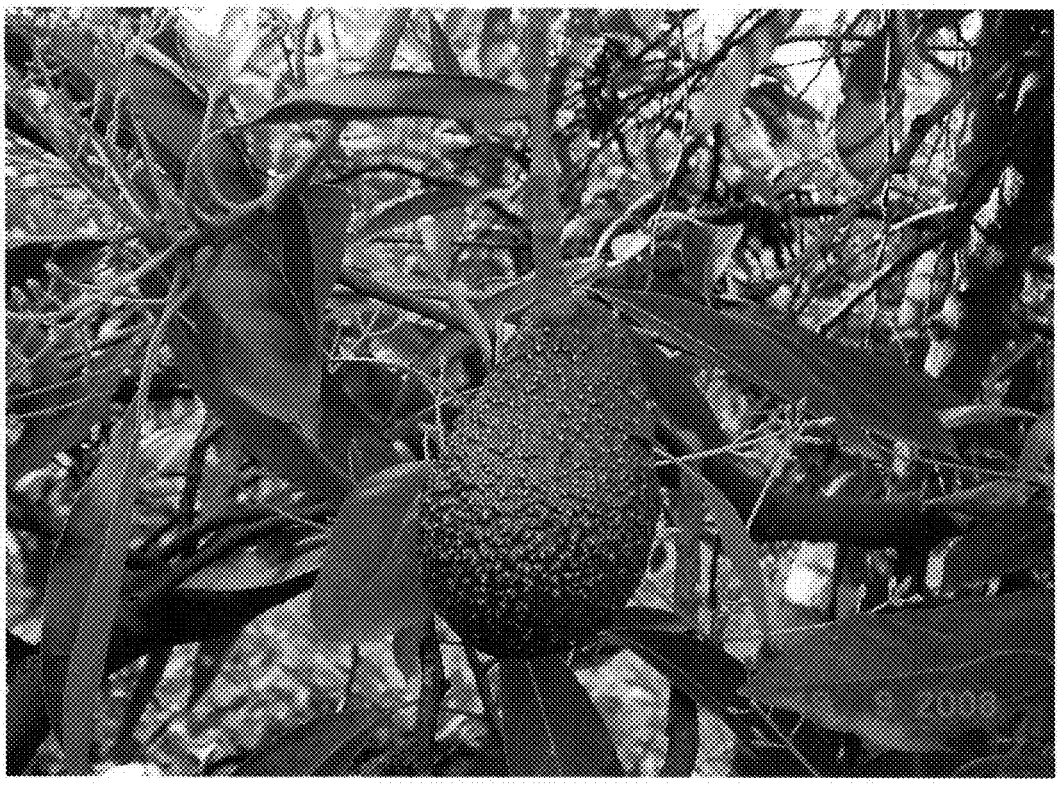
Figure 4:
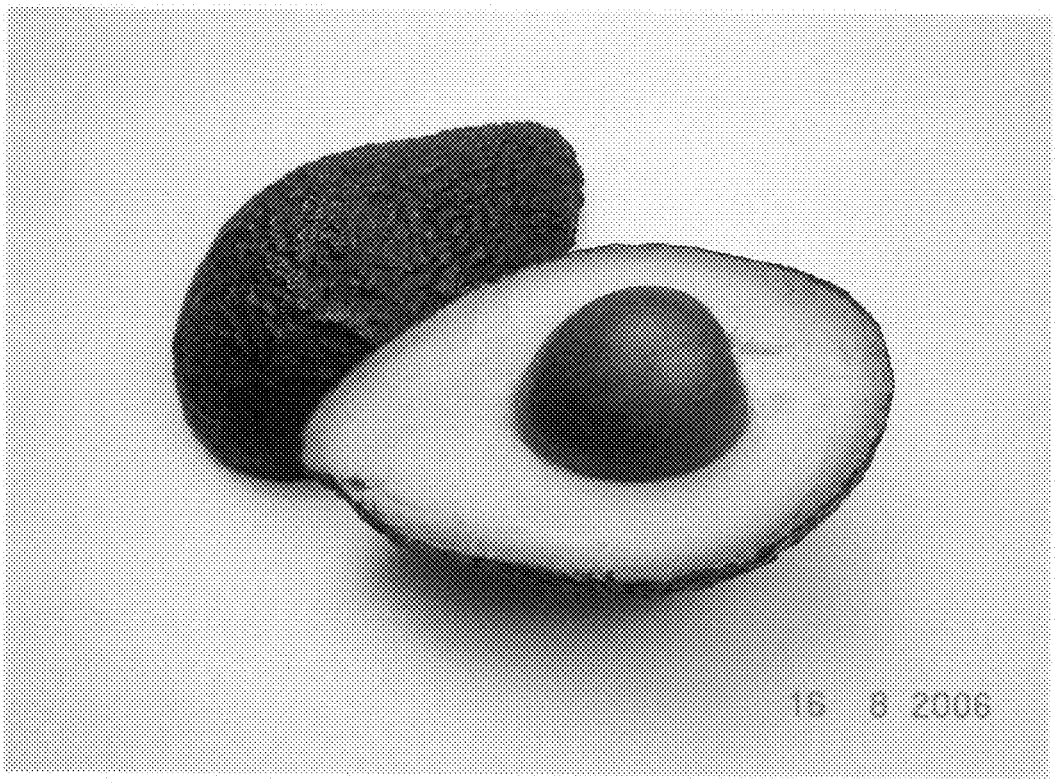

FIG. 1 shows a 'Maluma' tree;
FIG. 2 shows the leaves and inflorescence of 'Maluma';
FIG. 3 shows the fruit and leaves of 'Maluma'; and
FIG. 4 shows a sectioned fruit of 'Maluma'.

DETAILED BOTANICAL DESCRIPTION OF THE VARIETY

The following detailed botanical description is based on observations made during the 2008 growing season at Limpopo, Republic of South Africa of seven year old 'Maluma' trees grown on 'Duke 7' rootstock. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Height.*—5.5 m.
- *Spread.*—2.5 m at base.
- *Vigor.*—25 to 30 cm per year.
- *Branching habit.*—Axial-irregular.
- *Density.*—Open-intermediate.
- *Habit.*—Upright.
- *Hardiness.*—Tolerant to light frost, high wind tolerance, tolerant to lenticel damage.
- *Production.*—Productive, >20,000 kg per hectare per year.
- *Bearing.*—Precocious, annual.
- *Trunk.*—Circumference 55 cm at 30 cm from ground.
- *Bark texture.*—Grooves and ridges.
- *Bark color.*—Greyed-green 194B.
- *Trunk lenticels.*—Color greyed-green 194A, size 3 mm by 6 mm, density 150 per 100 $cm^2$.

Branch:
- *Primary branch diameter.*—80 mm.
- *Primary branch length.*—2.5 m.
- *Crotch angle.*—Obtuse (>90° ).
- *Texture.*—Light grooves and ridges.
- *Color, most recent flush.*—Green 134B.
- *Color, previous flush.*—Green 134A.
- *Lenticels.*—Color green 135A, size 0.5 by 2 mm, density 30 per $cm^2$.

Leaves:
- *Length.*—20 to 25 cm.
- *Width.*—5–6 cm.
- *Leaf shape.*—Oblanceolate.

*Tip shape.*—Acute.
*Base shape.*—Cuneate.
*Margin.*—Entire.
*Color.*—Upper surface green 135B, lower surface green 135D.
*Venation pattern.*—Secondary veins alternate, tertiary veins inconspicuous.
*Midvein size at base.*—Length 15 to 20 cm, diameter 2 mm, conspicuous.
*Midvein color.*—Upper surface yellow-green 144C, lower surface yellow-green 144D.
*Petiole.*—Length 4 to 6 cm, diameter 3 to 4 mm at axial end.
*Petiole color.*—Upper surface yellow-green 144C, lower surface 144D.
*Leaf arrangement.*—Alternate.
*Anthocyanin coloration.*—Present.

Flowers:
*Flower type.*—A type.
*Bud.*—Length 5 to 6 mm; width 4 to 5 mm; color yellow-orange 21C.
*Pedicel length.*—6 to 8 mm. Both determinate and indeterminate inflorescence, avg. 5 to 10 peduncles per inflorescence (panicle) with 10 to 20 flowers per peduncle.
*Peduncle length.*—6 to 8 cm. Flower abundance intermediate; Flower consists of pistil with stigma, style (straight) and ovary, 9 stamens (3 per whorl), 3 staminodes, nectaries (2 per inner stamen whorl), 3 petals, 3 sepals and a pedicel. Bloom date range mid-July to mid-September.

Fruit: Maturity date range early April to mid-June.
*Picking dates.*—First picking, week 12 (22% dry matter), last picking, week 24 (35% dry matter).
*Fruit size.*—Apical diameter 70 mm, axial diameter 35 mm, weight range 150 g to 400 g, with 250 g peak.
*Fruit shape.*—Pyriform, pedicel asymmetrical.
*Stem.*—Length 20 mm, diameter 14 mm, color yellow-green 144D.
*Skin.*—Unripe color green 135B, ripe color purple 79A, thickness 2 mm, texture leathery, semi-rough and pebbly, tenacity intermediate.
*Flesh.*—Color yellow-green 154C, texture when ripe smooth and buttery.
*Seed.*—Size 38 mm by 39 mm, weight 32 g, shape obovate with flattened base, skin color yellow 11C, cotyledon color yellow-green 153C.
*Eating quality.*—Excellent flavor and texture.

Storage characterisitics: Acceptable.
Shipping characteristics: Excellent.

I claim:

1. A new and distinct avocado tree substantially as described and illustrated herein.

* * * * *